US006582902B1

(12) United States Patent
Keene et al.

(10) Patent No.: US 6,582,902 B1
(45) Date of Patent: Jun. 24, 2003

(54) METHOD FOR DERIVING EPITOPES

(76) Inventors: Jack D. Keene, 6300 Garrett Rd., Durham, NC (US) 27707; Daniel J. Kenan, 2600 Englewood Ave., Durham, NC (US) 27705; Donald E. Tsai, 392 Linden Tarrace, Durham, NC (US) 27705

( * ) Notice: Subject to any disclaimer, the term of this patent is extended or adjusted under 35 U.S.C. 154(b) by 1289 days.

(21) Appl. No.: 08/862,337

(22) Filed: May 23, 1997

Related U.S. Application Data

(63) Continuation of application No. 08/447,196, filed on May 22, 1995, now abandoned, which is a continuation of application No. 07/956,693, filed on Sep. 30, 1992, now abandoned.

(51) Int. Cl.[7] .......................... C12Q 1/68; C12P 19/34; C07H 21/02; C07H 21/04
(52) U.S. Cl. .............................. 435/6; 435/5; 435/91.1; 435/91.2; 436/501; 536/22.1; 536/23.1; 536/24.3; 536/24.5
(58) Field of Search ................................ 435/5, 6, 91.1, 435/91.2; 436/501; 536/22.1, 23.1, 24.3, 24.5

(56) References Cited

U.S. PATENT DOCUMENTS 5,270,163 A 12/1993 Gold et al. ................... 435/6

FOREIGN PATENT DOCUMENTS

| WO | 8600991 | * | 2/1986 |
| WO | WO91/19813 | | 12/1991 |

OTHER PUBLICATIONS

Bock et al, (Feb. 1992), "Selection of single–stranded DNA molecules that bind and inhibit human thrombin", Nature 355:564–566.*
Naparstek et al, (1990), "Binding of anti–DNA antibodies and inhibition of glomerulonephritis in MRL–lpr/lpr mice by heparin", Arth. Rheum. 33(10):1554–1559.*
Reichlin et al, (1994), "Lupus autoantibodies to native DNA cross–react with the A and D SnRNP polypeptides", J. Clin. Invest. 93:443–449.*
Wright et al, (Aug. 1991), "Cyclic amplification and selection of targets (CASTing) for the myogenin consencus binding site", Mol. Cell. Biol. 11(8):4104–4110.*
D. P. Bartel et al., *Cell 67,* 529–536 (1991).
D.E. Tsai et al, *Nucleic Acids Research, 19,* 4931–4936 (1991).
A.D. Ellington et al., *Nature 346,* 818–822 (1990).
C. Turek et al., *Science 249,* 505–510 (1990).
S. Deutscher et al., *Proc. Natl. Acad. Sci. 85,* 3299–3303 (1988).
J. Wilusz et al., *The Journal of Biological Chemistry 261,* 5467–5472 (1986).
D.E. Tsai, et al., *In vitro selection of an* RNA *epitope immunologically cross–reactive with a peptide, Proc. Natl. Acad, Sci 89,* pp 8864–8868 (Oct. 1992).
D.E. Tsai & J.D. Keene, *In Vitro Selection of* RNA *Epitopes Using Autoimmune Patient Serum*[1] *, The Journal of Immunology, 150,* pp 1137–1145 (Feb. 1993).
S.M. Edgington, *Shape Space, Bio/Technology, 11* pp 285–289 (1993).
D.J. Kenan, *Exploring Molecular Diversity With Combinatorial Shape Libraries, Trends in Biochemical Sciences/19,* pp 57–64 (1994).

* cited by examiner

*Primary Examiner*—Jeffrey Fredman
(74) *Attorney, Agent, or Firm*—Myers Bigel Sibley & Sajovec, PA

(57) ABSTRACT

A method of generating a nucleic acid species which are immunologically cross-reactive with non-nucleic acid immunogens is disclosed. The method comprises combining an antigen binding protein which binds said immunogen with a degenerate pool of nucleic acid species, and then recovering a nucleic acid species bound by said antigen binding protein from said degenerate pool. Also disclosed are the nucleic acid species so made, along with the use thereof for tagging molecules for immunological detection, for detecting antibodies to predetermined non-nucleic acid immunogens, for blocking complex formation between an antigen binding protein and a non-nucleic acid immunogen, and for inducing an immune response to the immunogen in a human or animal subject. Preferred immunogens are peptides and preferred antigen binding proteins are antibodies.

22 Claims, 11 Drawing Sheets

|   | 1 | 2 | 3 | 4 | 5 |
|---|---|---|---|---|---| g10-U1-A ▶

METHOD FOR DERIVING EPITOPES

This is a continuation of application Ser. No. 08/447,196 filed May 22, 1995 now abandoned which is a continuation of application Ser. No. 07/956,693 filed on Sep. 30, 1992 now abandoned.

This invention was made with government support under a grant from the National Institutes of Health. The government has certain rights to this invention.

FIELD OF THE INVENTION

This invention relates to methods of making epitopes and nucleic acids embodying the epitopes so made.

BACKGROUND OF THE INVENTION

It is desireable to be able to probe and dissect the precise sites of antigen-antibody interaction. It is also desireable to find novel ways to detect antibodies and to inhibit specific antibody-antigen interactions. Furthermore, methods are needed that allow one to purify a monospecific antibody from a polyclonal serum without having to first purify the antigen.

It has not heretofore been possible to produce distinct and generally useful epitopes which react with a given antibody except in the case of epitope libraries. These peptide libraries depend upon expression of a random set of epitopes within the context of a larger protein. See, e.g., Scott et al., *Science* 249, 386 (1990); Cwirla et al., *Proc. Natl. Acad. Sci. USA* 87, 6378 (1990). This approach is restricted because it offers only proteinaceous ligands and is potentially compromised in contexts other than the fusion protein. In addition, "combinatorial peptide libraries" have been described which apply sequential positional determinations. See Houghten et al., *Nature* 454, 84 (1991). This procedure requires evaluation of the selected ligand at each step which, in turn, requires an exponential effort to define and select a specific epitope. Further, methods for screening degenerate pools of peptide sequences have been used which are not limited by proteinaceous context but are limited for logistical reasons (e.g., sophisticated synthesis and detection instruments are required). See Fodor et al., *Science* 251, 767 (1991); Geysen et al., *Proc. Natl. Acad. Sci. USA* 81, 3998 (1984).

S. Deutscher and J. Keene, *Proc. Natl. Acad. Sci. USA* 85, 3299 (1988) describe the selection and amplification of a nucleic acid ligand on U1 RNA from a randomized pool of nucleic acids (see also J. Wilusz and J. Keene, *J. Biol. Chem.* 261, 5467 (1986)). L. Gold and C. Tuerk, *Nucleic Acid Ligands*, PCT Appln. Publn No. WO 91/19813 (Dec. 26, 1991), describe the "evolution" of nucleic acid ligands and nucleic acid compounds refered to as "nucleic acid antibodies" (see also C. Tuerk and L. Gold, *Science* 249, 505–510 (1990)). A. Ellington and J. Szostak, *Nature* 346, 818–822 (1990), describe the binding of RNA molecules to organic dyes. D. Tsai et al., *Nucleic Acids Research* 19, 4931–4936 (1991), describe the binding of the U1-snRNP-A protein to specific RNA sequences in a degenerate pool of transcripts. D. Bartel et al., *Cell* 67, 529–563 (1991), describe the binding of the Rev protein of HIV-1 to a nucleic acid pool.

There has not heretofore been described a method by which an antibody can be employed to derive a nonproteinaceous mimetic ligand that binds to the same site on the antibody to which the original antigen bound.

SUMMARY OF THE INVENTION

A first aspect of the present invention is a method of generating a nucleic acid molecule which is immunologically cross-reactive with an immunogen, which immunogen is not a nucleic acid (e.g., a peptide). The method comprises combining an antigen binding protein which binds the immunogen (e.g., an antibody, a T cell receptor) with a degenerate pool of nucleic acid species, and then recovering a nucleic acid species bound by said binding protein from the degenerate pool.

A second aspect of the present invention is an isolated nucleic acid which inhibits complex formation between an antigen binding protein and an immunogen, which immunogen is not a nucleic acid. In one embodiment, the nucleic acid inhibits complex formation between a self peptide autoantigen and an antigen binding protein.

The foregoing and other objects and aspects of the present invention are explained in detail in the drawings herein and the specification set forth below.

DETAILED DESCRIPTION OF THE INVENTION

Amino acid sequences disclosed herein are presented in the amino to carboxy direction, from left to right. The amino and carboxy groups are not presented in the sequence.

Nucleotide sequences are presented herein by single strand only, in the 5' to 3' direction, from left to right.

The term "epitope," as used herein, refers to a portion of a molecule which has a three-dimensional structure on an exposed surface to which an antibody can specifically bind, whether in the context of said molecule or as a portion thereof.

The term "immunogen," as used herein, refers to a compound capable of eliciting an immune response, whether or not that compound is intentionally used to induce an immune response.

The term "antigen binding protein," as used herein, refers the members of the immunoglobulin superfamily. Members of the immunoglobulin superfamily include, but are not limited to, major histocompatibility complex molecules, cell adhesion molecules (including both neuronal cell adhesion molecules and cellular cell adhesion molecules) virus receptors such as picornavirus receptors (e.g., poliovirus receptors, rhinovirus receptors), growth factor receptors (e.g., interleukin receptors, lymphokine receptors), T cell receptors (e.g., alpha-beta class and gamma-delta class T cell receptors), and antibodies. Antibodies and T cell receptors are currently preferred.

The term "antibodies" as used herein refers to all types of immunoglobulins, including IgG, IgM, IgA, IgD, and IgE. The antibodies may be monoclonal or polyclonal and may be of any species of origin, including (for example) mouse, rat, rabbit, horse, or human, or may be chimeric antibodies. See, e.g., M. Walker et al., *Molec. Immunol.* 26, 403–11 (1989). Antibodies may be recombinant monoclonal antibodies produced according to the methods disclosed in Reading U.S. Pat. No. 4,474,893, or Cabilly et al., U.S. Pat. No. 4,816,567. Antibodies may also be chemically constructed according to the method disclosed in Segel et al., U.S. Pat. No. 4,676,980. The term antibodies further includes fragments which retain the specific binding characteristics of the antibody from which they are derived, with such fragments including, for example, Fab, F(ab')$_2$, and Fv fragments, and the corresponding fragments obtained from antibodies other than IgG. Such fragments are produced by known techniques. For example, monoclonal Fab fragments may be produced in *Escherichia coli* by recombinant techniques known to those skilled in the art. See, e.g., W. Huse, *Science* 246, 1275–81 (1989).

1. Methods of Making Nucleic Acid Epitopes

Figure 1:
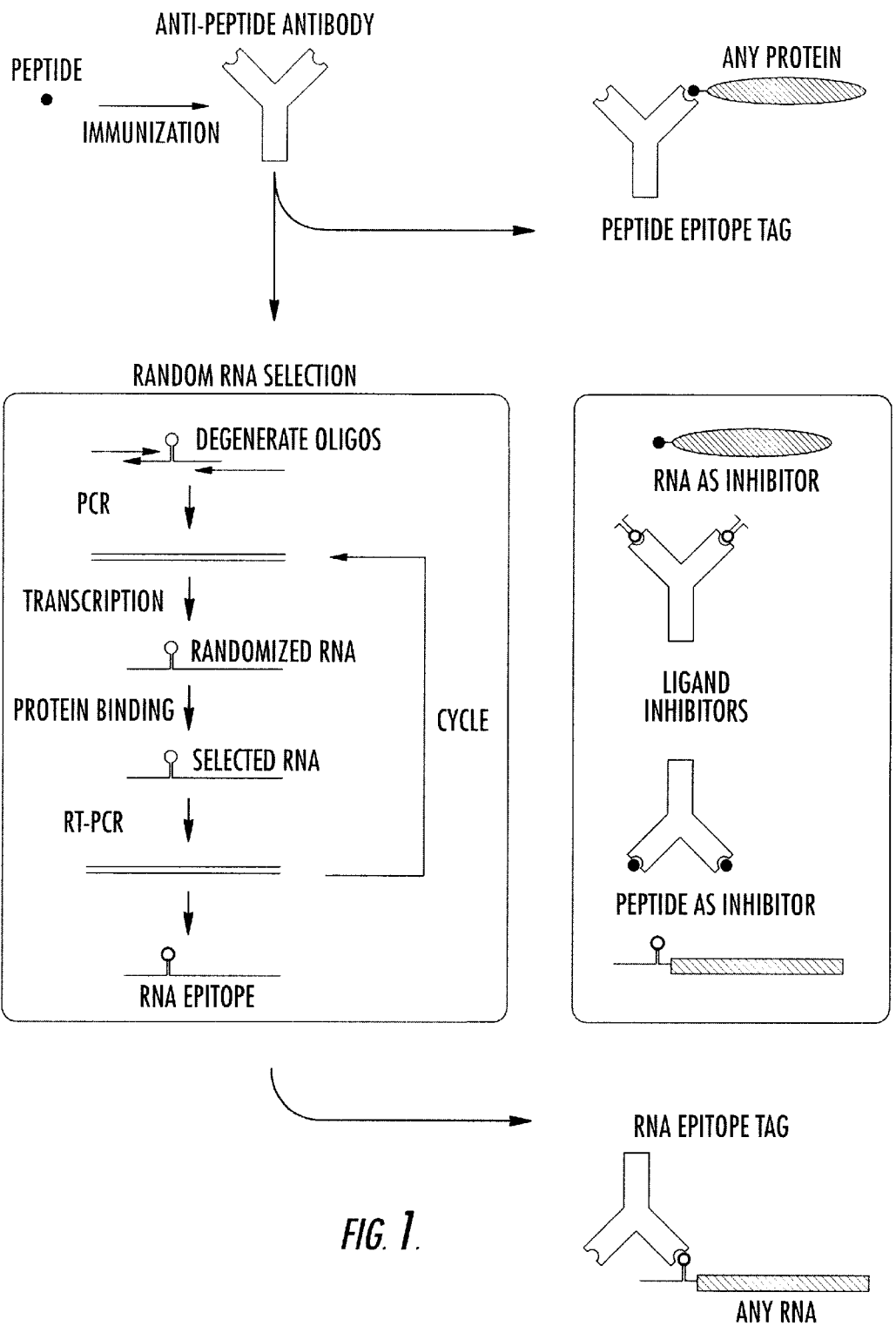
FIG. 1 is a schematic diagram of a process of the instant invention.

As noted above, the present invention provides a method of generating a nucleic acid molecule which is immunologically cross-reactive with a non-nucleic acid immunogen by combining an antigen binding protein which binds said immunogen with a degenerate pool of nucleic acid species (i.e., under conditions which permit the binding of a nucleic acid species to the antigen binding protein) and then recovering a nucleic acid species bound by the antigen binding protein from the degenerate pool. An embodiment of this method is schematically illustrated in FIG. 1, the steps of which are explained in detail below.

Initially, suitable anti-peptide antibodies (e.g., anti-g10 antibodies) are obtained. For example, polyclonal antibodies used to carry out the present invention may be produced by immunizing a suitable animal (e.g., rabbit, goat, etc.) with a non-nucleic acid immunogen antigen for which a nucleic acid epitope is desired, collecting immune serum from the animal, and removing the polyclonal antibodies from the immune serum, in accordance with known procedures. Monoclonal antibodies used to carry out the present invention may be produced in a hybridoma cell line according to the technique of Kohler and Milstein, *Nature* 265, 495–97 (1975). For example, a solution containing the appropriate antigen may be injected into a mouse and, after a sufficient time, the mouse sacrificed and spleen cells obtained. The spleen cells are then immortalized by fusing them with myeloma cells or with lymphoma cells, typically in the presence of polyethylene glycol, to produce hybridoma cells. The hybridoma cells are then grown in a suitable media and the supernatant screened for monoclonal antibodies having the desired specificity. Variations and refinements of these techniques can be employed to produce other types of antibodies, as noted above.

As an alternative to antibodies, other members of the immunoglobulin superfamily such as T cell receptors may be employed, as noted above. T cell receptors are structurally and functionally analogous to antibodies, and can be manipulated in much the same way as antibodies. See generally A. Williams and A. Barclay, *Ann. Rev. Immunol.* 6, 381–405 (1988); S. Brostoff and M. Howell, *Clin. Immunol. & Immunopathol.* 62, 1–7 (1992).

Non-nucleic acid immunogens other than peptides which may be employed include glycoproteins, fats, lipids, viruses (e.g., rhinovirus), polysaccharides, carbohydrates, and allergens. Allergens include pollen, mold, spores, insects, epidermal particles, dust, etc. See, e.g., Greer Laboratories, Inc., *Allergenic Extracts Allergy Supplies & Services,* 2–4 (Apr. 1, 1992)(Greer Laboratories, Inc., P.O. Box 800, Lenoir, N.C., USA 28645–0800; tel. 704-754-5327). Peptides are preferred, with the term "peptide" as used herein referring to a peptide as a discrete molecule or residing in a protein.

As an alternative to immunizing an animal with a known non-nucleic acid immunogen, antibodies may be collected from a human or animal subject without prior specific immunization to produce a nucleic acid epitope to an antigen binding protein where the native epitope bound by that antigen binding protein is unknown. For example, antibodies may be collected from human or animal subjects afflicted with autoimmune disease to produce a nucleic acid epitope which immunologically cross-reacts with the self peptide targeted by autoantibodies in the disorder. Examples of such autoimmune diseases in human subjects. include, but are not limited to, systemic lupus erythematosus, myasthenia gravis, and rheumatoid arthritis.

Once suitable antigen binding proteins are obtained, they are then combined with a degenerate pool of nucleic acid species. Such degenerate pools are known, and may be produced in accordance with known techniques. See, e.g., Blackwell et al., *Science* 250, 1104–1110 (1990); S. Deutscher and J. Keene, *Proc. Natl. Acad. Sci. USA* 85, 3299 (1988); Joyce et al., *Nucleic Acids Res.* 17, 711–722 (1989); Oliphant et al., *Methods Enzymol.* 155, 568 (1987). The pool may be formed of DNA molecules or RNA molecules, with pools of RNA molecules currently preferred. The nucleotide bases which form the pool may optionally be modified by methylation, O-methylation, provision of base analogues with atypical hydrogen bonding patterns, etc. In general, degenerate pools of nucleic acids comprise a plurality of distinct nucleic acid species in an aqueous solution. Typically, from 16 to $10^{10}$ distinct nucleic acid species are included in the pool, depending on the number of nucleotides being randomized. The precise number is not critical, though it is preferred that the number be sufficiently high to approach complete representation of all the possible members of the randomly represented set. Individual nucleic acid species within the pool will be 2, 3, 4, 5, or 6 nucleotides in length or more. There is no particular upper limit on the length of the nucleic acid species, with nucleic acids of 50, 100, or 200 or more nucleotides being suitable. The nucleic acid species may be linear or may possess some form of secondary structure, such as a stem and loop structure. Each nucleic acid species in the pool includes a degenerate segment of nucleotides, typically of 2, 3, or 4 up to about 25 or 100 nucleotides, in which each degenerate nucleotide position is randomly assigned both with respect to the other nucleotides in that segment of that species and with respect to nucleotides occupying the same position in other species in the degenerate pool. Note that "random" as used herein does not mean perfectly random: it merely means sufficiently random to provide a plurality of distinct species in the degenerate pool from which a particular species may be retrieved. Finally, each species in the degenerate pool may include non-random segments, such as primer segments or replication origins for amplification of the pool, though these segments may ultimately be removed from the final selected species as discussed below.

Combining the anti-peptide antigen binding protein with the degenerate pool may be facilitated by immobilizing the antigen binding protein on a solid support and contacting the degenerate pool (i.e., the aqueous solution carrying the degenerate pool) to the solid support, all in accordance with known techniques.

Typically, and as illustrated in FIG. 1, the step of combining the degenerate pool with the antigen binding protein is followed by the step of separating nucleic acid species bound to said solid support (e.g., by washing away any unbound nucleic acid species, then eluting nucleic acid species bound to the solid support); then producing a pool of complementary nucleic acids from said nucleic acid species separated from said solid support (e.g., reverse transcribing a pool of cDNAs from a DNA or RNA pool), then amplifying the pool of complementary nucleic acids to produce a subset degenerate pool of nucleic acid species, and then repeating the step of combining the degenerate pool of nucleic acid species with the antigen binding protein with the subset degenerate pool of nucleic acid species to produce a further subset degenerate pool of nucleic acids. This sequence of steps may be cyclically repeated to produce numerous subset degenerate pools, with the number of cycles typically being from three to nine, though a single cycle may in many cases be sufficient.

A separating step as described above preferably includes a wash step and an elution step. The wash step removes undesired nucleic acid species from the solid support, and the elution step removes the desired nucleic acid species from the solid support to provide the subset degenerate pool. The elution step may be carried out by any suitable means, such as phenol extraction. The separating step may be carried out at the same wash stringency at each cycle (i.e., as either a high stringency or low stringency wash), or the wash stringency may be changed between cycles (with stringency typically being adjusted from low stringency to high stringency as the cycles progress). In some cases, at least one high stringency wash step is included, and where the separating step is repeated, a high stringency wash step is included as the last separating step. Wash stringency may be increased by increasing the concentration of NaCl or urea in the wash buffer or by increasing the temperature of the wash buffer. Typically, buffers containing 150 mM NaCl at 4° C. are considered to provide lower wash stringency, buffers as above containing 0.3 M NaCl or greater, or 0.3 M urea or greater, or at temperatures greater than 20° C. are considered to provide intermediate to higher wash stringency, and buffers containing 0.5 M NaCl or greater, or 0.5 M urea or greater, or at temperatures greater than 37° C. are considered to provide higher wash stringency. Standard washing buffers also contain 0.05% nonidet P-40 and 50 mM Tris-HCl at pH 7.4, although the detergent, buffer, buffer salts, buffer concentration, and the pH are not critical and can be varied over a wide range. See, e.g., E. Harlow and D. Lane, Antibodies, A Laboratory Manual (Cold Spring Harbor Laboratory 1988): R. Bentley and J. Keene, *Mol. Cell. Biol.* 11, 1829 (1991).

The amplifying step may be carried out in vivo or in vitro by any suitable means. See generally D. Kwoh and T. Kwoh, *Am. Biotechnol. Lab.* 8, 14–25 (1990). In vivo amplification may be carried out by standard recombinant DNA techniques, such as by ligating cDNA produced as described above into a plasmid, and then taking that plasmid or pool thereof with inserts and transforming a bacterial culture therewith. See, e.g., J. Sambrook et al., Molecular Cloning, A Laboratory Manual (2d Ed. 1989) (Cold Spring Harbor Laboratory); J. Ma and M. Ptashne, *Cell* 51, 113–119 (1987); S. Deutscher and J. Keene, *Proc. Natl. Acad. Sci. USA* 85, 3299 (1988). Examples of suitable in vitro amplification techniques include, but are not limited to, polymerase chain reaction (see U.S. Pat. Nos. 4,683,202 and 4,683,195 to K. Mullis et al.), ligase chain reaction (see R. Weiss, *Science* 254, 1292 (1991)), strand displacement amplification (see G. Walker et al., *Proc. Natl. Acad. Sci. USA* 89, 392–396 (1992); G. Walker et al., *Nucleic Acids Res.* 20, 1691–1696 (1992)), transcription-based amplification (see D. Kwoh et al., *Proc. Natl. Acad Sci. USA* 86, 1173–1177 (1989)), self-sustained sequence replication (or "3SR")(see J. Guatelli et al., *Proc. Natl. Acad. Sci. USA* 87, 1874–1878 (1990)), the Qβ replicase system (see P. Lizardi et al., *BioTechnology* 6, 1197–1202 (1988)), nucleic acid sequence-based amplification (or "NASBA") (see R. Lewis, *Genetic Engineering News* 12 (9), 1 (1992)), the repair chain reaction (or "RCR") (see R. Lewis, supra), and boomerang DNA amplification (or "BDA")(see R. Lewis, supra).

Once a desired nucleic acid species is recovered, it may be amplified and/or sequenced and synthesized in accordance with known techniques. A complementary nucleic acid (e.g., a cDNA) to the nucleic acid species may be produced by reverse transcription and the desired nucleic acid species produced in greater quantities by recombinant techniques. The immunological cross-reactivity of the recovered nucleic acid species with the non-nucleic acid immunogen it mimics may be confirmed by suitable immunoassay, such as blocking assays or competition experiments, carried out in accordance with known techniques.

The foregoing method provides an isolated nucleic acid which inhibits complex formation between an antigen binding protein and a non-nucleic acid immunogen. Binding of the nucleic acid to such an antigen binding protein can be routinely determined in a standard competition assay in vitro, with nucleic acids of the invention having dissociation constants ($K_d$s) of $10^{-5}$, $10^{-7}$ or $10^{-8}$ up to $10^{-12}$ or $10^{-14}$ moles per liter. The format of competition assay is not critical, though enzyme-linked immunosorbent assay (ELISA) or radioimmunoassay (RIA) are particularly convenient. Nucleic acids of the invention have association constants ($K_a$s) which make them useful as inhibitors of the binding of non-nucleic acid immunogens to antigen binding proteins (such as antibodies), with the $K_a$s for such nucleic acids ranging from $10^5$, $10^7$, $10^8$, or $10^9$ up to $10^{10}$ or $10^{12}$ liters per mole, with these values being determinable in the same manner as given above with respect to $K_d$s. The nucleic acid itself may mimic any of a broad variety of non-nucleic acid immunogens: for example, one embodiment of the foregoing is an isolated nucleic acid which inhibits complex formation between a self peptide autoantigen and an antigen binding protein, wherein said antigen binding protein is from a human or animal subject which expresses said self peptide. Such antigen binding proteins may be obtained from human subjects afflicted with an autoimmune disease, as noted above.

As with the nucleic acid species in the degenerate pool, isolated nucleic acids of the present invention may be of any length, typically of from 2, 3, 4, 5, or 6 nucleotides in length or more. Again there is no particular upper limit on the length of the isolated nucleic acid, with nucleic acids of 50, 100, or 200 or more nucleotides being suitable. As above, the isolated nucleic acid may be linear or may possess some form of higher order structure, such as a stem and loop structure. Further, the isolated nucleic acid may be modified from that initially retrieved from the degenerate pool, such as by removing primer segments or other portions thereof which are not critical for binding, or by making minor modifications to the structure of one or more of the individual nucleotides in the nucleic acid itself such as methylation, O-methylation, provision of nucleotide analogues with atypical patterns of hydrogen bonding, other modifications to prevent nucleophilic attack on the phosphodiester bond, and the like.

2. Uses for Nucleic Acid Epitopes

Isolated nucleic acids of the invention can be used in a variety of ways. For example, the isolated nucleic acid may be conjugated, either directly or indirectly and either covalently or non-covalently, to a molecule to be tagged thereby (i.e., a "tagged molecule"). The tagged molecule itself may be, for example, a protein or a heterologous nucleic acid. The tagged molecule can then be detected with antigen binding proteins, particularly antibodies, known to bind that isolated nucleic acid.

Nucleic acids of the invention may be used in methods of detecting an antigen binding protein which binds a predetermined non-nucleic acid immunogen. Such methods comprise contacting a biological sample suspected of containing the antigen binding protein to a nucleic acid, which nucleic acid is capable of inhibiting complex formation between the antigen binding protein and said non-nucleic acid immunogen, under conditions which permit the formation of a reaction product; and then detecting the presence or absence of the reaction product. Biological samples taken from human or animal subjects for use in this method are generally biological fluids such as serum, blood plasma, or ascites fluid. In the alternative, the sample taken from the subject can be a tissue sample (e.g., biopsy tissue; scrapings; etc.). Any suitable assay format can be used to carry out the detection of the reaction product, examples being radioimmunoassay, immunofluorescence methods, enzyme-linked immunoassays, and the like. Those skilled in the art will be familiar with numerous specific immunoassay formats and variations thereof which may be useful for carrying out the method disclosed herein. See generally E. Maggio, *Enzyme-Immunoassay*, (1980)(CRC Press, Inc., Boca Raton, Fla.).

Nucleic acids of the present invention may be used to produce an immune response to a non-nucleic acid immunogen in a human or animal (e.g., dog, cat, horse, goat, rabbit) subject. In this case, the nucleic acid serves as a surrogate immunogen for the non-nucleic acid immunogen. The method comprises administering a nucleic acid to the subject, which nucleic acid is capable of inhibiting complex formation between an antigen binding protein and the immunogen, with the nucleic acid being administered in an amount effective to induce an immune response in said animal to said immunogen. Techniques for enhancing the immunogenicity of the nucleic acid which are known in the art may, if desired, be employed. Subjects may be administered nucleic acids for this purpose to simply raise stocks of antibodies, or for therapeutic purposes to subjects in need of such treatment. Administration to a subject may be carried out by any suitable means, such as by subcutaneous injection, intravenous injection, intraperitoneal injection, and nasal spray. The amount of nucleic acid administered will depend upon factors such as route of administration, species, use of booster administrations, etc., but is generally between 50 micrograms to 5 milligrams per kilogram subject body weight, and more typically is between 50 micrograms and 200 micrograms per kilogram subject body weight.

Nucleic acids of the invention may be employed in methods of blocking complex formation between a non-nucleic acid immunogen and an antigen binding protein (again, typically an antibody) which binds the non-nucleic acid immunogen. Such methods comprise contacting the antigen binding protein to a nucleic acid, which nucleic acid inhibits complex formation between the antigen binding protein and the non-nucleic acid immunogen. The contacting step may be carried out in vitro (again typically by combining constituents in an aqueous solution), or may be carried out in vivo in a human or animal subject. Where carried out in vivo, the subject, dosage, route of administration, and other parameters may be as given above in connection with a method of inducing an immune response. Where carried out in vitro, again, numerous different formats for carrying out such blocking experiments will be known to those skilled in the art, as also discussed above.

Nucleic acids may be prepared for administration to a subject as a pharmaceutical composition comprising the nucleic acid in a pharmaceutically acceptable carrier. Preparation is typically carried out by intimately admixing the nucleic acid with the carrier. The nucleic acid is included in an amount sufficient to achieve the intended effect: i.e., induce an immune response or block complex formation between an antigen binding protein and an immunogen, as explained above. Pharmaceutically acceptable carriers may be solid or liquid carriers, such as sterile pyrogen-free phosphate-buffered saline solution. The carrier may optionally contain one or more adjuvants, such as aluminum hydroxide, aluminum phosphate, plant and animal oils, etc. In addition, the vaccine formulation may contain one or more stabilizer, exemplary being carbohydrates such as sorbitol, mannitol, starch, sucrose, dextran, and glucose, proteins such as albumin or casein, and buffers such as alkaline metal phosphates and the like.

3. Generation of Nucleic Acid Sets Useful as Polyvalent Vaccines

The techniques described above may be used to provide a method of generating a set of nucleic acid species useful as immunogens, where at least two members of the set are not immunologically cross-reactive with one another. By "immunologically cross-reactive" is meant that the cross-reactive compounds or species bind to the same antigen binding protein at the same site (including overlapping sites) with the binding affinities give herein (e.g., they compete for binding with one another). The method comprises collecting a plurality of antigen binding proteins from a human or animal subject, which antigen binding proteins are either antibodies or T cell receptors; combining the antigen binding proteins with a degenerate pool of nucleic acid species; and then recovering a plurality of nucleic acid species bound by the antigen binding proteins from the degenerate pool to produce the set. Preferably, the nucleic acid species are immunologically cross-reactive with compounds which are not nucleic acids, and at least two members of the set are immunologically cross-reactive with different immunogens. Such methods are particularly useful for developing polyvalent vaccines, i.e., vaccines capable of inducing an immune response to different epitopes on a common immunogen and/or vaccines capable of inducing an immune response to different immunogens.

The collecting step may be carried out by any suitable means, such as by harvesting T cell lymphocytes from the subject, by collecting immune serum from the subject, or both. Note that the type of immune response elicited by the vaccine can be biased towards cellular or humoral by means of the type of antigen binding protein collected. If a vaccine for a particular disease is desired the antigen binding proteins may be collected from a subject afflicted with the disease or by immunizing a suitable subject with an immunogen for that disease prior to the collecting step. Note that this method provides the advantage that an infectious agent or toxin need not be isolated or identified in order to generate a vaccine against it. The technique may be employed with any disease, including diseases of viral, bacterial, protozoan, or other microbial origin.

In an alternative embodiment, antigen binding proteins collected from a plurality of subjects, all previously afflicted with the same disease or infected with the same disease-causing organism, are pooled to ultimately provide a polyvalent vaccine directed against numerous variants or serotypes of that disease. For example, one or more elderly subjects who lived through the influenza epidepmic of 1918 will have the combined immunological experience to resist any potential challenge by the swine flu virus, H1N1. The combined immunological repertoire of this population of individuals, which includes antibodies to multiple determinants of the virus such as the surface antigens, hemagglutinin (H1) and neuraminidase (N1), can be captured from their pooled sera using this invention and that repertoire passed by immunization of an immunologically naive subject(s) using the polyvalent vaccine. Further, the entire immunological repertoire of any population which has developed immune resistance to any pathogen, known or unknown, could be similarly passaged using such polyvalent vaccines derived from their combined sera. It is one advantage of this invention that the vaccine recipients need not be subject to exposure to the pathogen or to any materials extracted from a pathogen. The nucleic acid vaccine is rendered pure by simple extraction using any of several standard procedures such as emulsification in phenol.

Another example of the practice of this invention is using rhinoviruses which cause the common cold. It has not been possible to develop satisfactory vaccines to rhinoviruses because approximately 30 different, but related serotypes exist. The viral antigenic determinants can change abruptly and mutate in order to escape immune surveillance. However, in the combined experience of a population of individuals resides a record of immunological response to all of the various serotypes of the rhinovirus. Thus, the present invention will allow the derivation of a polyvalent vaccine to rhinovirus using the combined sera of a population of individuals experienced with infection by the many serotypes of rhinovirus. Such a vaccine will provide broad protection to the recipient for all rhinovirus challenges.

This invention embodies an additional advantage for the production of a polyvalent vaccine in that the selected nucleic acid mimetics will contain in the sub pool structural variants of the original immunogen which can be used to immunize the subject against unanticipated variants of a pathogen. For example, the protozoan agent of African sleeping sickness, *Trypanosoma brucei*, contains on its surface VSG antigens that can undergo spontaneous antigen switching allowing the pathogen to escape immune surveillance. The present invention provides for the derivation of polyvalent nucleic acid vaccines which mimic subtle variations of the original antigen. Thus, some selected ligands in the vaccine resemble the exact original non-nucleic immunogen while others resemble subtle variations of the original immunogen.

These methods provide a set of isolated nucleic acids, each of which nucleic acids inhibits complex formation between an antigen binding protein and an immunogen, wherein the antigen binding protein is either an antibody or a T cell receptor, and wherein at least two members of the set do not bind to the same antigen binding protein. Members of the set will have the characteristics as given above: e.g., bind to the antigen binding protein at a $K_d$ of from $10^{-5}$ or $10^{-7}$ to $10^{-14}$ moles per liter. The set may be provided in an aqueous carrier solution, may be provided in the form of a cDNA library encoding the set as described above, or may be provided in a pharmaceutically acceptable carrier as described above. The set is essentially free of other nucleic acids which do not possess such binding characteristics, though other ingredients can of course be added to the set which do not detract from the function thereof.

4. Mimetic Conformational Selection for Rational Drug Design

The techniques described above can also be adapted for generating tools for the rational design of drug compounds. Such techniques are particularly useful where other structural information on the drug compound is unavailable. In general, the method generates a plurality of nucleic acid species which are immunologically cross-reactive with a drug compound (which compound is not a nucleic acid, and which compound possesses at least two epitopes). The method comprises immunizing an animal with the drug compound according to methods described above, then collecting antigen binding proteins that bind the compound, then combining the antigen binding proteins with a degenerate pool of nucleic acid species, and then recovering a plurality of nucleic acid molecules bound by the antigen binding protein from the degenerate pool, wherein at least two of the nucleic acid species do not bind to the same antigen binding protein. The method may be employed with any drug compound which presents a plurality of epitopes thereon, including (but not limited to) peptides, glycoproteins, fats, lipids, polysaccharides, and carbohydrates, including chemical analogues thereof.

The foregoing techniques provide a set of isolated nucleic acid species which inhibits complex formation between an antigen binding protein and a drug compound as described above, wherein at least two of the nucleic acid species do not bind to the same antigen binding protein. The characteristics of the members of the set are as given above: i.e., they bind to the antigen binding protein at a $K_d$ of from $10^{-5}$ or $10^{-7}$ to $10^{-14}$ moles per liter. The set may be provided in an aqueous carrier solution, as a cDNA library encoding the same, or in a pharmaceutical carrier. The set may be screened itself for drug analogs, or may be used to vaccinate a suitable host subject as discussed above to generate additional complementary mimetic surface ligands. Again, the set is essentially free of other nucleic acids which do not possess such binding characteristics, though other ingredients can of course be added to the set which do not detract from the function thereof.

Mimetic conformational selection can be used to improve the biological efficacy of a compound such as a receptor binding molecule, by providing a pool of structural variants which themselves possess biological activity as agonists or antagonists. For example, insulin which binds to an insulin receptor can serve as the immunogen and insulin-binding antibodies can be collected for use in conformational selection. Mimetic nucleic acid ligands selected using the antibodies are structural analogus of insulin and can also be utilized as functional analogs of insulin in biological assays and therapeutic regimens. Furthermore, structural analysis of selected mimetic ligands by any of several known methods (i.e., co-crystallographic analysis) will provide a means to correlate variations in biological function of the mimetic molecule with its structural features. For example, mimetic nucleic acid ligands that always display receptor agonist activity should conserve certain structural features. These surfaces can be modeled against the original drug compound in order to rationally engineer optimal drug design.

The foregoing is explained in greater detail in the following non-limiting examples.

EXAMPLE 1

Preparation and Characterization of an Antiserum Reactive with the g10 Peptide

A thirteen amino acid peptide was synthesized representing the amino-terminus of g10-fusion proteins expressed from the Studier T7 expression vectors (F. Studier et al., *Meth. Enzym.* 185, 60–89 (1991)) (peptide sequence: MASMTGGQQMGRC-carboxyl amide (SEQ ID NO:11), purchased from Multiple Peptide Systems). The first eleven amino acids represent the gene 10 protein, the arginine is encoded by the linker in these expression vectors, and the cysteine was incorporated for conjugation to the carrier. The peptide was coupled to keyhole limpet hemocyanin (Sigma) using the crosslinker MBS (3-maleimidobenzoyl-N-hydroxysuccinimide ester, Boehringer Mannheim Biochemicals). A high-titer antiserum was obtained from rabbits immunized with the peptide-carrier conjugate in accordance with standard techniques. The specificity of the antiserum was characterized using Western blot and immunoprecipitation methods previously reported (J. Chambers and J. Keene, *Proc. Natl. Acad. Sci. USA* 82, 2115–2119 (1985); R. Bentley and J. Keene, *Mol. Cell. Biol.* 11, 1829–1839 (1991)), with details as set forth below. Recombinant proteins were expressed in bacteria using the Studier T7 system as published previously (supra). Western blots were probed with various sera diluted 1:2000 and decorated with [$^{125}$I] protein A. [$^{35}$S]-labeled proteins were prepared by in vitro transcription of cDNA constructs with T7 RNA polymerase followed by translation in rabbit reticulocyte lysates.

Figure 3A:
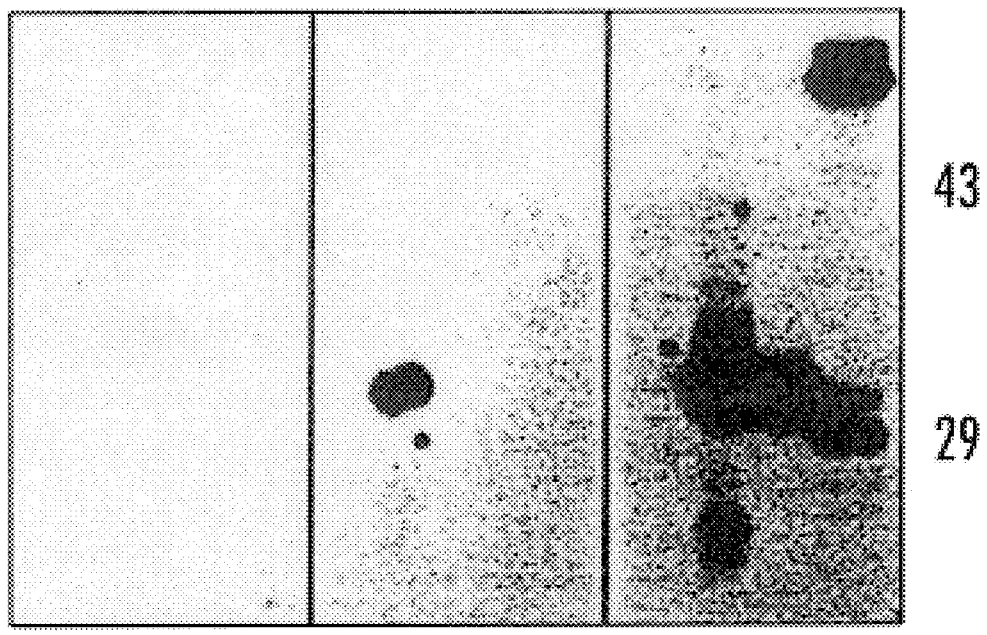
FIG. 3 shows the g10 fusion peptide used as an epitope tag. Panel A: Western blot of *E. coli* extracts containing various U1-A protein constructs. All extracts were produced from induced *E. coli* cells containing recombinant pET-8c T7 expression vectors in accordance with known techniques. See F. Studier et al., *Meth. Enzym.* 185, 60–89 (1991). U1-A cDNA was cloned into pET-8c either attached or not attached to the g10 peptide. Lanes: 1, 5 and 9: the pET-8c vector alone; 2, 6 and 10: g10-U1-A protein; 3, 7 and 11: U1-A protein; 4, 8 and 12: total HeLa cell extracts. Lanes 1–4 were probed with pre-immune rabbit serum; lanes 5–8 were probed with anti-g10 serum; and lanes 9–12 were probed with a U1/U2-specific autoimmune serum (patient EW). EW reacts with U1 RNA, U1-70K (70 kDa), U1-A (31 kDa) and U2-A' (28.4 kDa) (lane 12). Panel B: Immunoprecipitation and competition analysis of [$^{35}$S]-methionine-labeled U1-A and g10-U1-A proteins expressed by in vitro transcription, and subsequent translation in rabbit reticulocyte lysates. Lanes: 1 and 2 show the amount of U1-A and g10-U1-A translation product, respectively, added to each immunoprecipitation reaction; 3: blank; 4 and 5: U1-A and g10-U1-A precipitated with serum EW (reactive with U1-A); 6 and 7: U1-A and g10-U1-A, respectively, precipitated with anti-g10 serum. In lanes 8–12, g10-U1-A was precipitated with anti-g10 serum in the presence of varying amounts of competitors as follows: lanes 8–11 contained the g10 peptide at concentrations of 27.8, 83.3, 250 and 750 nM, respectively; lane 12 contained a control peptide (sequence GKSRGFAFVEFK-amide) (SEQ ID NO:4) at a concentration of 25 mM. The faint lower band in all lanes represents either a degradation product or a premature translation termination product and is seen consistently in U1-A translations.
Figure 3B:
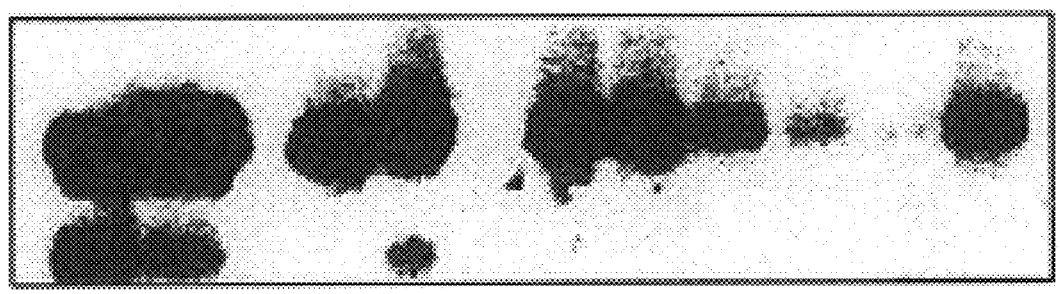

FIG. 3 demonstrates that the serum was specific for proteins containing the g10 fusion peptide as assayed by immunoblot and immunoprecipitation. FIG. 3A shows recognition by the anti-g1 serum of g10-tagged U1-snRNP A protein (g10-U1-A) in Western blot analysis. The anti-g10 serum reacted with only the g10-U1-A fusion protein (FIG.

3A, lane 6), but not with recombinant U1-A (lane 7) or authentic HeLa cell U1-A (lane 8), while a control anti-U1-A serum reacted with over-expressed U1-A and g10-U1-A, as well as with authentic HeLa cell U1-A (compare FIG. 3A, lanes 6–8 with 10–12). Anti-g10 reactivity with g10-U1-A protein was analyzed also by immunoprecipitation. As expected, the anti-g10 serum precipitated g10-U1-A fusion protein (FIG. 3B, lane 7), but not U1-A protein (lane 6). Anti-g10 antibody binding could be inhibited by excess free g10 peptide (FIG. 3B, lanes 8–11), but not by a control peptide (lane 12), further demonstrating that the interaction was specific for the g10 peptide sequence. Taken together, these results demonstrate that the g10 fusion peptide can function as an epitope tag recognized by the anti-g10 serum.

A more demanding test of an epitope tag is recognition of the tagged molecule within the context of a macromolecular complex. Among the potential complications of using an epitope tag are its interference in assembly of a complex or its inaccessibility within an assembled complex. Previous studies have used the g10 tag to immunoprecipitate RNP complexes formed in vitro between g10-U1-A and U1RNA. Other RNP complexes analyzed using the g10 epitope include those formed by U1-70K, U2-B", U2-A', and Ro-RNP 60 kD. RNP particles formed by these tagged proteins in vivo also are accessible to recognition of the epitope by the anti-g10 serum as assessed by immunoprecipitation and immunofluorescence (data not shown).

EXAMPLE 2

Figure 2:
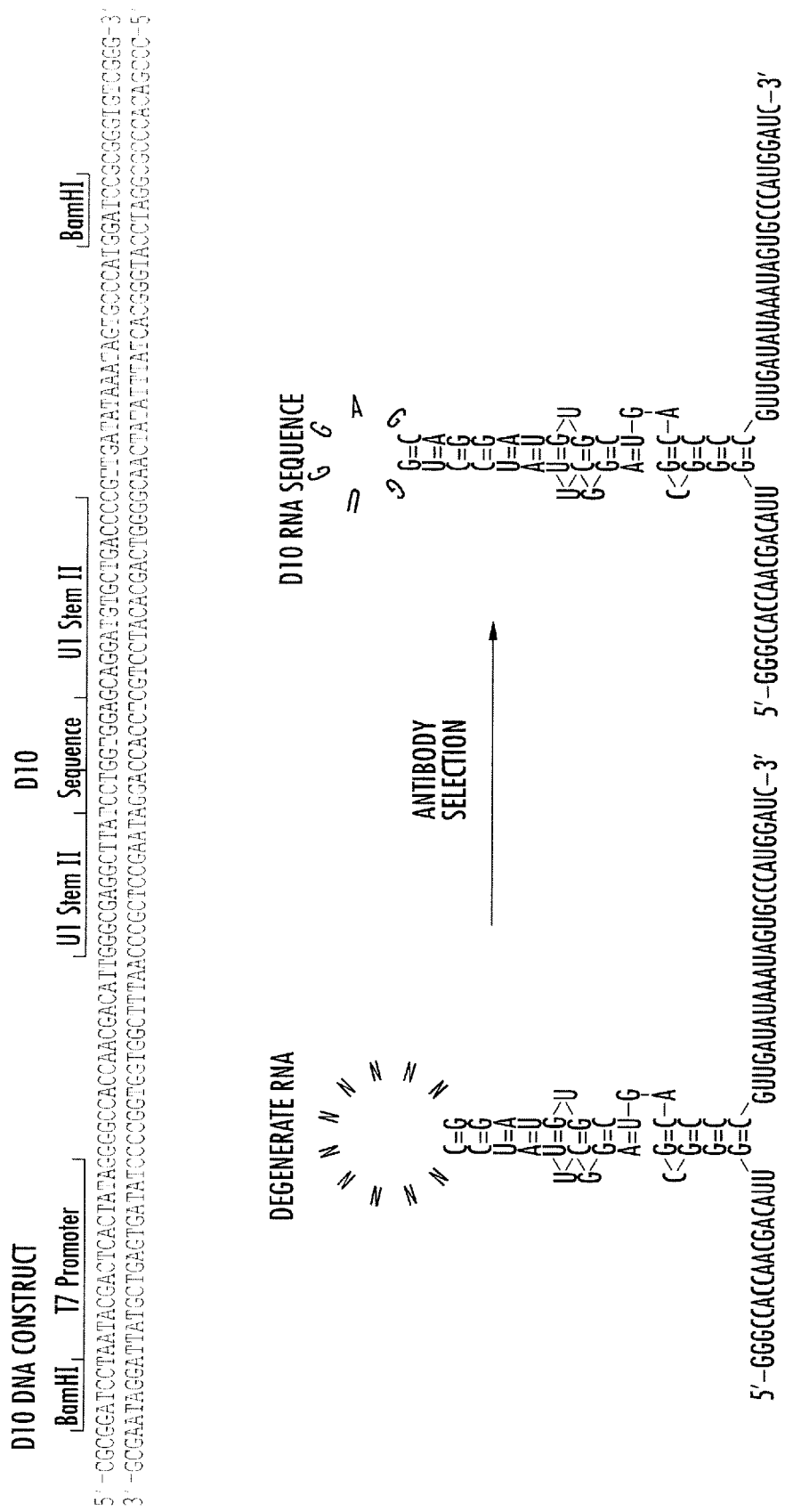
FIG. 2 shows D10 DNA construct (upper)(SEQ ID NO:1) and the degenerate RNA transcript (lower)(SEQ ID NO:2) used to select the D10 RNA epitope (SEQ ID NO:3). Degenerate nucleotide positions in the predicted RNA secondary structure are represented by "N." BamHI restriction sites, the T7 promoter, complementary regions representing U1 stem II and the D10 loop sequence are indicated.

Selection of Specifically Bound RNA by Immunoprecipitation with g10 Peptide Antibody Whereas the g10 peptide is a useful epitope tag for analyzing complexes containing protein, an RNA epitope tag would be equally useful for studying complexes containing RNA. The anti-g10 serum was presented with a degenerate pool of RNA containing 1,048,576 unique species, assuming incorporation of four different nucleotides at 10 randomized loop positions (FIG. 2). These RNAs were transcribed from approximately $1 \times 10^{11}$ molecules of degenerate oligodeoxynucleotide template (D. Tsai et al., *Nucl. Acids Res.* 19, 4931–4936 (1991)). Assuming that most templates are transcribed at least once, all possible RNA species should be redundantly represented.

RNA was prepared by in vitro transcription of PCR-generated templates in accordance with known techniques (D. Tsai et al., *Nucl. Acids Res.* 19, 4931–4936 (1991)). The transcripts were immunoprecipitated with the anti-g10 serum as follows: Protein A Sepharose beads (Sigma, 4 mg per 50 ml reaction) were washed in NT2 buffer (50 mM Tris [pH 7.4], 150 mM NaCl, 0.05% Nonidet P-40) (C. Query et al., *Cell* 57, 89–101 (1989)), mixed with 2 ml of anti-g10 serum, incubated on ice for 10 min, and washed in NT2. The beads were then resuspended in 100 ml KNET+buffer (50 mM Tris pH 7.4, 80 mM NaCl, 20 mM KCl, 2 mM EGTA, 0.05% Nonidet P-40, 1 mM $MgCl_2$, 2.5% polyvinyl alcohol, 40 units/ml of RNasin, 5 mg/ml of poly(A) RNA, and 0.2% VRC, 50 mg/ml tRNA and 50 mg/ml BSA) (C. Query et al., supra). RNA was added and the reactions incubated at 37° C. for 7 minutes. The pellets were washed five times with NT2buffer. Higher stringency washes included 0.5 M urea in the first wash. RNA was recovered by phenol extraction and ethanol precipitation. RNAs were reverse transcribed and cDNAs subjected to PCR amplification as described previously (D. Tsai et al., *Nucl. Acids Res.* 19, 4931–4936 (1991)). The amplified template was used to repeat the above cycle for two additional rounds. The final PCR product was digested with BamHI, cloned and sequenced.

Low stringency selection yielded five different but related species (data not shown). On the other hand, after three cycles of antibody selection with high stringency washing, a single RNA species, D10, was obtained in 45 out of 45 isolates.

Figure 4:
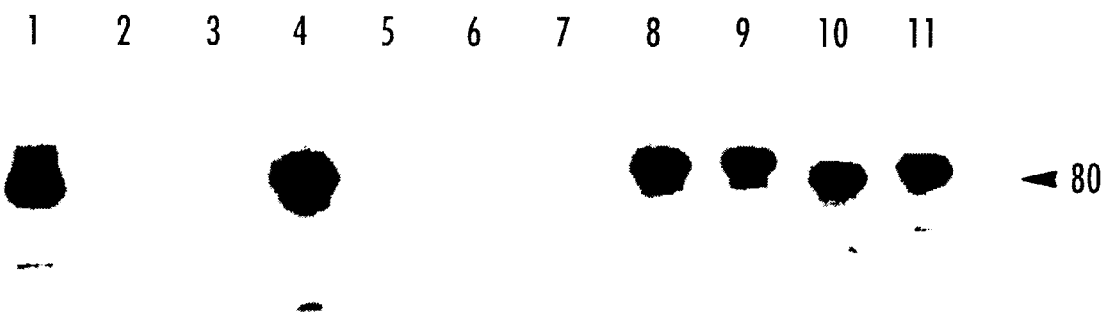
FIG. 4 shows the D10 RNA epitope binds specifically to g10 antibodies. Various antisera were used to precipitate either [32P] labeled in vitro transcribed D10 RNA or control transcripts. Bound RNA was analyzed on a denaturing 6% polyacrylamide gel by autoradiography. Lanes 1–4 are precipitations of D10 RNA with the following antisera: 1, anti-g10 serum; 2, preimmune serum; 3, no antibody; 4, anti-g10 serum. Other transcripts were precipitated with the anti-g10 serum as follows: 5, a control RNA identical to the D10 epitope but with loop sequence 5'-CACCAUAUAA-3' (SEQ ID NO:5); 6, an unrelated RNA; 7, an RNA containing the loop sequence 5'-CUGACCCCGU-3'(SEQ ID NO:6); 8–11, supernatants from the immunoprecipitations shown in lanes 4–7, diluted to approximate radioactive equivalents.

To rule out the possibility of nonspecific RNA binding, [$^{32}$P]-D10 RNA precipitations were performed with either protein A Sepharose beads alone, pre-immune serum, or anti-g10 serum. The D10 RNA bound only to the anti-g10 serum (FIG. 4, lane 1), confirming that binding is specific for the post-immune antiserum. Immunoprecipitation experiments with various RNA species suggest that the anti-g10 serum is specific for the D10 RNA sequence. For example, an unrelated RNA was not recognized (FIG. 4, lane 6), nor were RNAs containing the same stem but with different loop sequences (lanes 5 and 7). These findings demonstrate that the antibody binds a specific RNA structure or sequence.

EXAMPLE 3

D10 RNA Binds to the g10 Antibody Antigen Recognition Site

Although the D10 RNA is recognized by the anti-g10 serum, the selection procedure theoretically could recover RNA bound to any surface of any antibody molecule in the serum. Since the pre-immune serum showed no reactivity towards the D10 RNA, the most likely RNA-binding surface is the antigen-combining site of the g10-specific antibodies. This possibility was tested by competition experiments using the g10 peptide and the D10 RNA.

Figure 5A:
FIG. 5 shows competition analysis of g10 peptide and D10 RNA epitopes for binding by the g10 antibodies. [$^{32}$P] labeled in vitro transcribed D10 RNA or [$^{35}$S] labeled in vitro translated g10 fusion protein (g10-U1A) was immunoprecipitated by the anti-g10 serum in the presence of various competitors. D10 RNA and g10 fusion protein bound in the immunoprecipitations were analyzed using denaturing polyacrylamide gels and autoradiography. Panel A: D10 RNA immunoprecipitations with: 1, no competitor; 2, no g10 antiserum added; 3, 125 mg of g10 peptide; 4, 125 mg of bovine serum albumin; 5, 125 mg of control peptide (sequence ETPEEREERRR) (SEQ ID NO:7). Panel B: D10 immunoprecipitations after incubation with increasing amounts of g10 peptide. Lanes: 1, no competitor; 2, 37 nM; 3, 74 nM; 4, 148 nM; 5, 222 nM; 6, 444 nM. Panel C: immunoprecipitations of a g10 containing fusion protein (g10-U1-A) using various competitors. Lanes: 1, no competitor; 2, preimmune rabbit serum; 3, 7.4 nM g10 peptide; 4, 0.7 nM D10 RNA; 5, 0.7 nM unrelated RNA (cDNA encoding loop sequence: ACGTTCGTCG)(SEQ ID NO:8). Panel D: immunoprecipitation of g10-U1A fusion protein after incubation with increasing amounts of D10 RNA. Lanes: 1, no competitor; 2, 0.0175 nM; 3, 0.035 nM; 4, 0.35 nM; 5, 0.7 nM; 6, 1.05 nM.
Figure 5B:

Competition experiments were performed by addition of the various competitors to [$^{32}$P] labeled RNA or [$^{35}$S] labeled in vitro translated g10-snRNP-A fusion protein prior to immunoprecipitation. Bound RNAs were analyzed on 6% denaturing acrylamide gels and proteins on 10% SDS-PAGE gels, followed by autoradiography. Antibody-RNA complexes were formed in the presence of competitor g10 peptide or control peptide (FIG. 5A), or with increasing amounts of g10 peptide (FIG. 5B), and uncompeted RNA was recovered by immunoprecipitation. As expected, neither bovine serum albumin nor an unrelated peptide showed any effect on D10 RNA precipitation by the anti-g10 serum (FIG. 5A, lanes 4 and 5). However, increasing amounts of g10 peptide inhibited RNA binding by the antiserum (FIG. 5B, lanes 1–6).

Figure 5C:
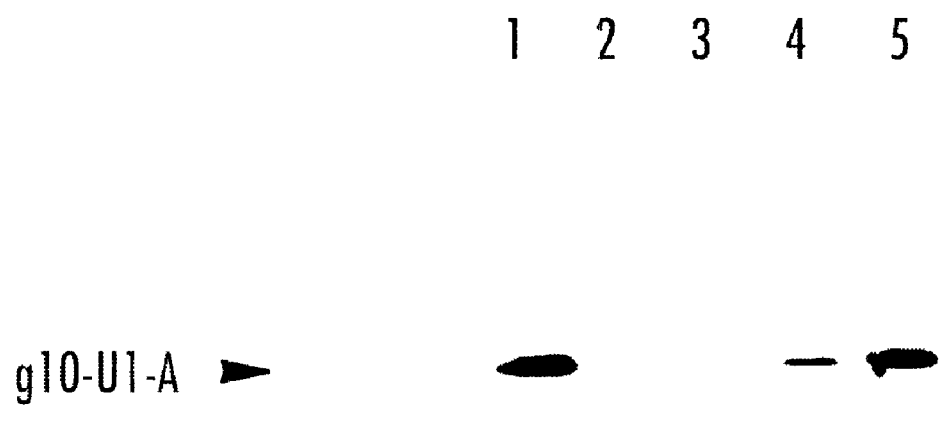
Figure 5D:
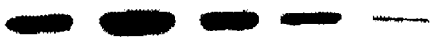

Similarly, the D10 RNA was examined for its ability to inhibit complex formation between a g10 fusion protein and the g10-reactive antibodies. The D10 RNA was able to compete with the g10 fusion protein for binding to the antibody (FIG. 5C, lane 4). An unrelated RNA was not able to compete for the antibody combining site (FIG. 5C, lane 5). In addition, increasing amounts of D10 RNA were able to progressively compete with an [$^{35}$S] labeled g10 fusion protein (FIG. 5D, lanes 1–6). These results are consistent with competition between two antigens for the same or overlapping antigen-binding sites on the antibody. The finding that essentially all of the reactive antibodies recognized both the RNA and peptide epitopes implies that the immune response was mounted against a single epitope on the g10 peptide and that the D10 RNA contains a single cross-reactive epitope.

EXAMPLE 4

Use of the D10 RNA as an Epitope Tag

Figure 6A:
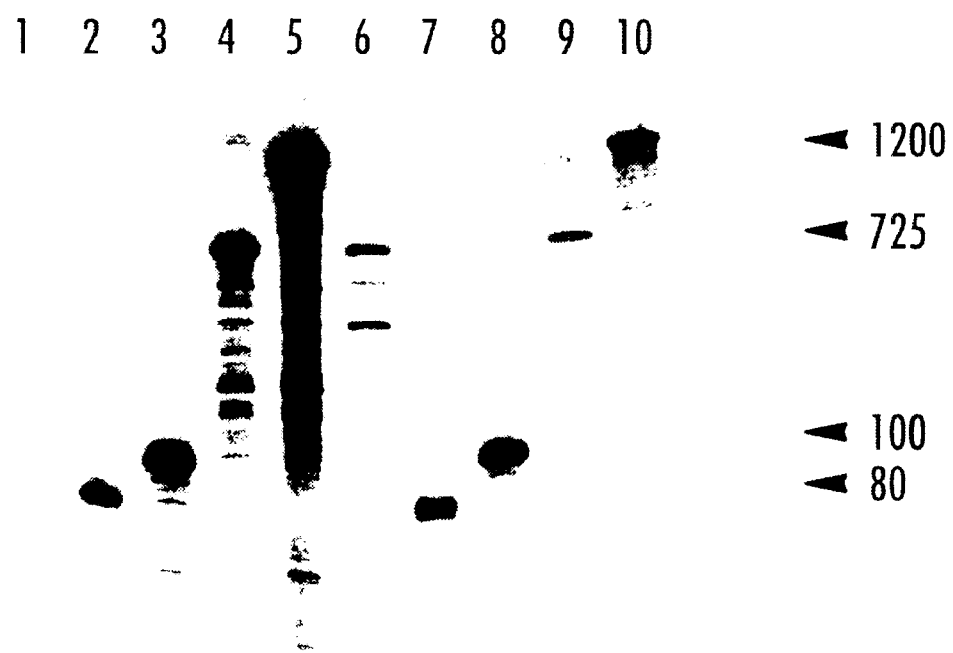
FIG. 6 shows immunoprecipitation of RNAs tagged with the D10 RNA epitope. In vitro transcribed [$^{32}$P] radiolabeled RNA was immunoprecipitated with anti-g10 serum or with an anti-U1 RNA serum (EW). Bound RNA was analyzed using a denaturing 6% acrylamide gel and autoradiography: Panel A: The D10 DNA construct (FIG. 2) was cloned into the BamHI site of PGEM-3zf (+) to produce tagged vector RNA, and transcripts with different 3'termini were generated with SP6 RNA polymerase. The anti-g10 serum was used to precipitate the following transcripts (lanes): 1, U1 RNA (negative control); 2, D10 RNA; 3–5, increasing lengths of D10 tagged vector RNA; 6–10, supernatants from lanes 1–5, respectively. Approximate nucleotide sizes are indicated by arrows. Panel B: U1 RNA was tagged with the D10 epitope by replacing loop III, sequence CAAAUGU (SEQ ID NO:9), with the sequence UGGUGGAGCA (SEQ ID NO:10) (construct U1-3Dx). Lanes: 1, total deproteinized HeLa cell RNA; 2, total HeLa cell RNA mixed with exogenous NEU1 transcript (wild-type U1 RNA sequence plus extra 3' nucleotides from the U1 gene); 3, total HeLa cell RNA mixed with exogenous U1-3Dx, plus extra 3' nucleotides; 4–6, RNA mixtures from lanes 1–3 precipitated with an anti-U1 RNA serum (EW); 7–9, RNA mixtures from lanes 1–3 precipitated with the anti-g10 serum; 10–11, same as lane 9, but U1-3Dx was diluted 1:3 and 1:9, respectively; 12–14, RNA mixtures from lanes 1–3, except that total HeLa cell extract was used instead of HeLa cell RNA and precipitated with anti-g10 serum; 15–17, RNA mixtures from lanes 1–3, precipitated with pre-immune serum. Only 0.5% of the total RNA mixtures were loaded in lanes 1–3, and these lanes were exposed three times longer than the other lanes. U1-3Dx consistently produced a doublet as observed in lanes 3, 6, 9–11, and 14. For unexplained reasons, a small amount of endogenous U1 RNA was detected in the presence of total HeLa cell extract (lanes 12–14).

To test whether D10 can serve as an epitope tag for RNA, the D10 DNA sequence (FIG. 2) was cloned into pGEM- 3zf(+) and various length transcription templates produced by truncation 3' to the D10 epitope. RNA was synthesized in vitro from these templates, and the anti-g10 serum was used to immunoprecipitate the D10-tagged pGEM-3zf(+) RNAs. All fusion RNAs were precipitated by the anti-g10 serum (FIG. 6A, lanes 2–5), while a control RNA was not precipitated (lane 1). Therefore, the D10 sequence is functional as an RNA epitope tag in these contexts.

The complexity of RNA sequences within the pool of artificially randomized 10-mer loops approaches that of RNA sequences within a HeLa cell; however, recognition of an RNA epitope within the cellular milieu may encounter different constraints than recognition within a pool of in vitro transcripts. In an effort to assess the utility of the D10 epitope in cellular extracts, we immunoprecipitated D10-tagged in vitro transcripts mixed with total HeLa cell RNA or with HeLa cell extracts.

[$^{32}$P] labeled HeLa cell extracts and [$^{32}$P] labeled deproteinized HeLa cell RNA were prepared in accordance with known techniques (R. Bentley and J. Keene, *Mol. Cell. Biol.* 11, 1829–1839 (1991)). [$^{32}$P] labeled in vitro transcripts were mixed with either HeLa cell extract or HeLa cell RNA under the D10 binding conditions described above. The anti-RNA reactivities in the anti-g10 serum and in the anti-U1 RNA patient serum (EW) were normalized by using 1 ml of a (1:5) dilution of serum EW and 10 ml of the anti-g10 serum. Antibody-RNA complexes were analyzed as described above.

Figure 6B:
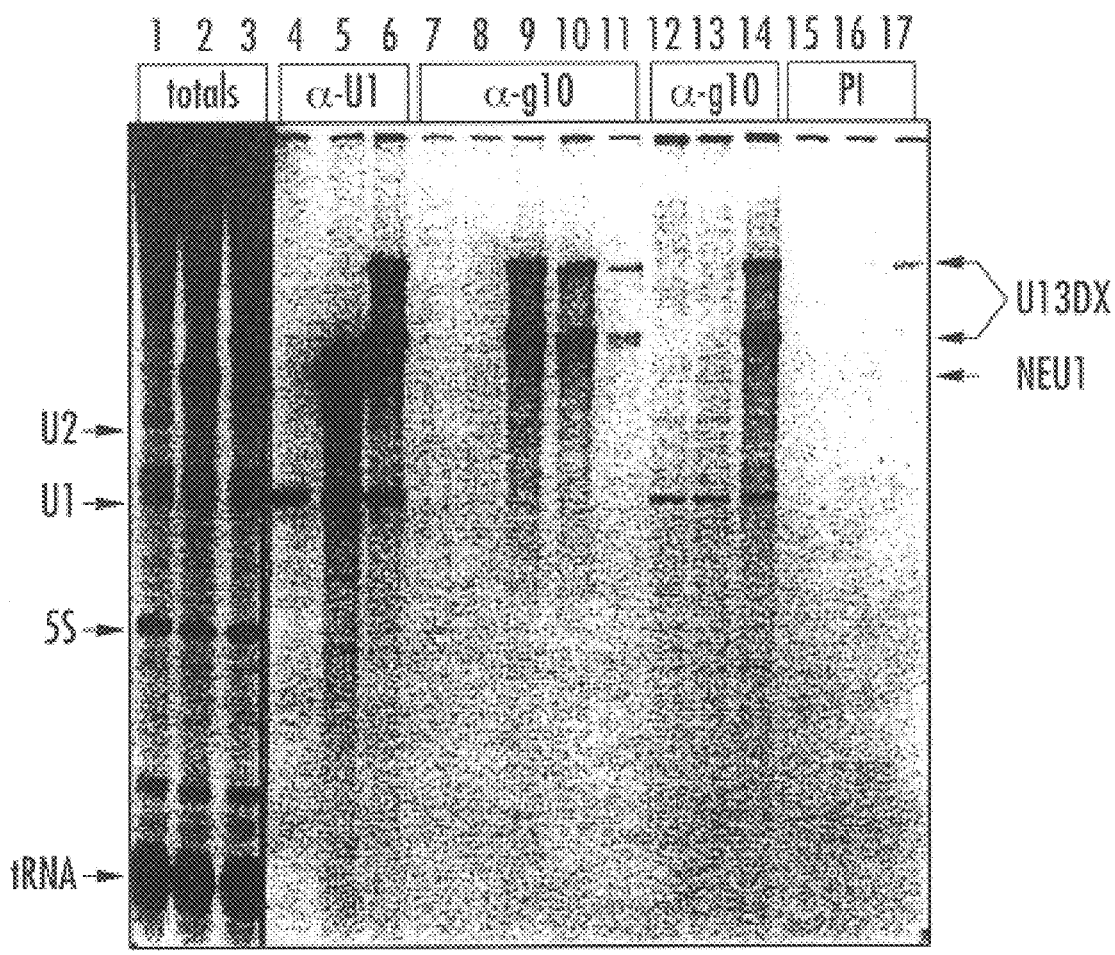

A construct of U1 RNA in which the loop III was replaced by the loop of D10 RNA, termed U1-3Dx (gift of J. Snedeker), was efficiently precipitated by the anti-g10 serum in the presence of total HeLa cell RNA (FIG. 6B, lanes 9–11) and extract (lane 14). In contrast, transcripts of exogenous NEU1 RNA (see legend to FIG. 6B) were not immunoprecipitated by the anti-g10 serum (FIG. 6B, lane 8 and 13); however, they were recognized by a patient serum, EW, that binds the second stem-loop of U1 RNA (lane 5). Furthermore, the anti-g10 serum was not reactive with HeLa cell RNA (FIG. 6B, lane 7). These results show that the D10 epitope can be recognized in the presence of total cellular RNA and proteins. Furthermore, the fact that the U1-3Dx construct was recognized by the anti-g10 serum identifies a minimal sequence required for antibody recognition as CCUGGUGGAGCAGG (SEQ ID NO:12), in the context of a stem.

EXAMPLE 5

Autoimmune Serum from an SLE Patient Binds RNA Sequences from a Degenerate Pool

This example demonstrates that antibodies taken directly from a subject afflicted with an autoimmune disease can be used to generate nucleic acid species which bind thereto.

A degenerate pool of RNA sequences is created using synthetic DNA oligomers that are randomized in either of three different contexts representing linear unstructured RNA or in the framework of the natural U1 stem II, from positions 50–89, containing degenerate loops of 10 or 13 nucleotides as described in detail previously (D. Tsai et al., *Nucl. Acids Res.* 19, 4931–4936 (1991)). All three RNA structural contexts share identical PCR primer regions at the 5'and 3'termini. A selection procedure is performed consisting of three cycles of successive transcription, RNA immunoprecipitation with serum from a patient afflicted with systemic lupus erythematosus (SLE), reverse transcription, and PCR as described above. Sequencing of multiple clones, each representing a selected RNA species, reveals several RNA species which bind to antibodies in EW patient serum.

The foregoing examples are illustrative of the present invention, and are not to be construed as limiting thereof. The invention is defined by the following claims, with equivalents of the claims to be included therein.

That which is claimed is:

1. A method of generating a nucleic acid species which is immunologically cross-reactive with an immunogen, which immunogen is not a nucleic acid, said method comprising:
   combining an antigen binding protein which binds said immunogen with a degenerate pool of nucleic acid species; and then
   recovering a nucleic acid species bound by said antigen binding protein from said degenerate pool, with said nucleic acid and said immunogen binding to the same antigen recognition site on said antibody.

2. A method according to claim 1, wherein said antigen binding protein is selected from the group consisting of antibodies and T cell receptors.

3. A method according to claim 1, wherein said antigen binding protein is an anti-g10 antibody.

4. A method according to claim 1, wherein said immunogen is selected from the group consisting of peptides, glycoproteins, fats, lipids, polysaccharides, carbohydrates, viruses and allergens.

5. A method according to claim 1, wherein said degenerate pool of nucleic acid species is a degenerate pool of RNA species.

6. A method according to claim 1, wherein said degenerate pool of nucleic acid species comprises a plurality of nucleic acids having from 2 to 200 nucleotides.

7. A method according to claim 1, wherein said degenerate pool of nucleic acid species comprises a plurality of nucleic acids having from 4 to 100 nucleotides.

8. A method according to claim 1, wherein said degenerate pool of nucleic acid species comprises a plurality of nucleic acids having a degenerate segment of from 2 to 25 nucleotides.

9. A method according to claim 1, wherein said degenerate pool of nucleic acid species comprises a plurality of linear nucleic acids.

10. A method according to claim 1, wherein said degenerate pool of nucleic acid species comprises a plurality of nucleic acids having a stem and loop configuration.

11. A method according to claim 1, wherein said antigen binding protein is immobilized on a solid support, and said recovering step is carried out by contacting said degenerate pool of nucleic acid species to said solid support.

12. A method of generating a set of nucleic acid species useful as immunogens, and wherein at least two members of said set are not immunologically cross-reactive with one another, said method comprising:
    collecting a plurality of antigen binding proteins from a human or animal subject, which antigen binding proteins are selected from the group consisting of antibodies and T cell receptors;
    combining said antigen binding proteins with a degenerate pool of nucleic acid species; and then
    recovering a plurality of nucleic acid species bound by said antigen binding proteins from said degenerate pool to produce said set.

13. A method according to claim 12, wherein a plurality of said nucleic acid species are immunologically cross-reactive with compounds which are not nucleic acids.

14. A method according to claim 12, wherein said antigen binding proteins are immobilized on a solid support, and said recovering step is carried out by contacting said degenerate pool of nucleic acid species to said solid support.

15. A method according to claim 14, wherein said contacting step is followed by the steps of:
    separating nucleic acid species bound to said solid support; then
    producing a pool of complementary nucleic acids from said nucleic acid species separated from said solid support; then
    amplifying said pool of complementary nucleic acids to produce a subset degenerate pool of nucleic acid species which subset degenerate pool comprises said plurality of nucleic acid species; and then
    repeating said step of contacting a degenerate pool of nucleic acid species to said solid support with said subset degenerate pool of nucleic acid species.

16. A method of generating a plurality of nucleic acid species which are immunologically cross-reactive with a drug compound and are useful for rational drug design, which compound is not a nucleic acid, said method comprising:
    combining an antigen binding protein which binds said compound with a degenerate pool of nucleic acid species; and then
    recovering a plurality of nucleic acid molecules bound by said antigen binding protein from said degenerate pool
    and wherein at least two of said nucleic acid species do not bind to the same antigen binding protein.

17. A method according to claim 16, wherein said antigen binding protein is selected from the group consisting of antibodies and T cell receptors.

18. A method according to claim 16, wherein said compound is selected from the group consisting of peptides, glycoproteins, fats, lipids, polysaccharides, and carbohydrates.

19. A method according to claim 16, wherein said antigen binding protein is immobilized on a solid support, and said recovering step is carried out by contacting said degenerate pool of nucleic acid species to said solid support.

20. A method according to claim 16, wherein said contacting step is followed by the steps of:
    separating nucleic acid species bound to said solid support; then
    producing a pool of complementary nucleic acids from said nucleic acid species separated from said solid support; then
    amplifying said pool of complementary nucleic acids to produce a subset degenerate pool of nucleic acid species, which subset degenerate pool comprises said plurality of nucleic acid species; and then repeating said step of contacting a degenerate pool of nucleic acid species to said solid support with said subset degenerate pool of nucleic acid species.

21. A method of generating a nucleic acid species which is immunologically cross-reactive with an immunogen, which immunogen is not a nucleic acid, said method comprising:

combining an antigen binding protein which binds said immunogen with a degenerate pool of nucleic acid species; and then recovering a nucleic acid species bound by said antigen binding protein from said degenerate pool, with said nucleic acid and said immunogen binding to the same antigen recognition site on said antibody;

wherein said antigen binding protein is immobilized on a solid support and said recovering step is carried out by contacting said degenerate pool of nucleic acid species to said solid support;

and wherein said contacting step is followed by the steps of:

separating nucleic acid species bound to said solid support; then producing a pool of complementary nucleic acids from said nucleic acid species separated from said solid support; then amplifying said pool of complementary nucleic acids to produce a subset degenerate pool of nucleic acid species; and then repeating said step of contacting a degenerate pool of nucleic acid species to said solid support with said subset degenerate pool of nucleic acid species.

22. A method according to claim 21, further comprising the step of assaying the immunological cross-reactivity of said immunogen and said nucleic acid species.

* * * * *

UNITED STATES PATENT AND TRADEMARK OFFICE
CERTIFICATE OF CORRECTION

PATENT NO. : 6,582,902 B1
DATED : June 24, 2003
INVENTOR(S) : Keene et al.

It is certified that error appears in the above-identified patent and that said Letters Patent is hereby corrected as shown below:

<u>Title page,</u>
Item [56], References Cited, FOREIGN PATENT DOCUMENTS, please add the following reference that was omitted:
-- WO 92/14843      9/3/1992      Toole et al. --

Signed and Sealed this

Twenty-seventh Day of April, 2004

JON W. DUDAS
*Acting Director of the United States Patent and Trademark Office*

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
          (A) LENGTH: 121 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:1:

```
CGCGGATCCT AATACGACTC ACTATAGGGG CCACCAACGA CATTGGGCGA GGCTTATCCT     60

GGTGGAGCAG GATGTGCTGA CCCCGTTGAT ATAAATAGTG CCCATGGATC CGCGGGTGTC    120

G                                                                    121
```

(2) INFORMATION FOR SEQ ID NO:2:

(i) SEQUENCE CHARACTERISTICS:
          (A) LENGTH: 83 base pairs
          (B) TYPE: nucleic acid (C) STRANDEDNESS: single
            (D) TOPOLOGY: linear (ii) MOLECULE TYPE: rRNA (xi) SEQUENCE DESCRIPTION: SEQ ID NO:2:

GGGCCACCAA CGACAUUGGG CGAGGCUUAU CCNNNNNNNN NNGGAUGUGC UGACCCCGUU      60

GAUAUAAAUA GUGCCCAUGG AUC                                            83

(2) INFORMATION FOR SEQ ID NO:3:

(i) SEQUENCE CHARACTERISTICS:
            (A) LENGTH: 83 base pairs
            (B) TYPE: nucleic acid
            (C) STRANDEDNESS: single
            (D) TOPOLOGY: linear (ii) MOLECULE TYPE: rRNA (xi) SEQUENCE DESCRIPTION: SEQ ID NO:3:

GGGCCACCAA CGACAUUGGG CGAGGCUUAU CCUGGUGGAG CAGGAUGUGC UGACCCCGUU      60

GAUAUAAAUA GUGCCCAUGG AUC                                            83

(2) INFORMATION FOR SEQ ID NO:4:

(i) SEQUENCE CHARACTERISTICS:
            (A) LENGTH: 12 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:4:

Gly Lys Ser Arg Gly Phe Ala Phe Val Glu Phe Lys
      1               5                  10

(2) INFORMATION FOR SEQ ID NO:5:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: rRNA (xi) SEQUENCE DESCRIPTION: SEQ ID NO:5:

CACCAUAUAA                                                           10

(2) INFORMATION FOR SEQ ID NO:6:

(i) SEQUENCE CHARACTERISTICS:
            (A) LENGTH: 10 base pairs
            (B) TYPE: nucleic acid
            (C) STRANDEDNESS: single
            (D) TOPOLOGY: linear (ii) MOLECULE TYPE: rRNA (xi) SEQUENCE DESCRIPTION: SEQ ID NO:6:

CUGACCCCGU                                                           10

(2) INFORMATION FOR SEQ ID NO:7:

(i) SEQUENCE CHARACTERISTICS:
            (A) LENGTH: 11 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

Glu Thr Pro Glu Glu Arg Glu Glu Arg Arg
    1               5                   10

(2) INFORMATION FOR SEQ ID NO:8:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

ACGTTCGTCG                                                              10

(2) INFORMATION FOR SEQ ID NO:9:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:9:

CAAAUGU                                                                  7

(2) INFORMATION FOR SEQ ID NO:10:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: rRNA (xi) SEQUENCE DESCRIPTION: SEQ ID NO:10:

UGGUGGAGCA                                                              10

(2) INFORMATION FOR SEQ ID NO:11:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Met Ala Ser Met Thr Gly Gly Gln Gln Met Gly Arg Cys
    1               5                   10

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single -continued

```
        (D) TOPOLOGY: linear (ii) MOLECULE TYPE: rRNA (xi) SEQUENCE DESCRIPTION: SEQ ID NO:12:

CCUGGUGGAG CAGG                                                              14
```